United States Patent [19]

Vu et al.

[11] Patent Number: 5,256,562
[45] Date of Patent: Oct. 26, 1993

[54] METHOD FOR MANUFACTURING A SEMICONDUCTOR DEVICE USING A CIRCUIT TRANSFER FILM

[75] Inventors: Duy-Phach Vu, Taunton; Brenda D. Dingle; Jason E. Dingle, both of Mansfield; Ngwe Cheong, Boston, all of Mass.

[73] Assignee: Kopin Corporation, Taunton, Mass.

[21] Appl. No.: 970,675

[22] Filed: Nov. 4, 1992

Related U.S. Application Data

[63] Continuation-in-part of Ser. No. 874,588, Apr. 24, 1992, which is a continuation-in-part of Ser. No. 834,849, Feb. 13, 1992, which is a continuation-in-part of Ser. No. 636,602, Dec. 31, 1990, Pat. No. 5,206,749, and a continuation-in-part of Ser. No. 643,552, Jan. 18, 1991.

[51] Int. Cl.$^5$ .................... H01L 21/20; H01L 21/22; H01L 21/304; H01L 21/52
[52] U.S. Cl. .................... 437/86; 437/205; 437/208; 437/966; 437/974; 156/DIG. 88
[58] Field of Search ................ 437/205, 208, 86, 966, 437/974; 156/DIG. 88

[56] References Cited

U.S. PATENT DOCUMENTS

| | | | |
|---|---|---|---|
| 3,658,618 | 4/1972 | Gramann | 437/205 |
| 4,226,649 | 10/1980 | Davey et al. | 437/86 |
| 4,255,208 | 3/1981 | Deutscher et al. | 156/DIG. 88 |
| 4,321,747 | 3/1982 | Takemura et al. | 437/974 |
| 4,575,854 | 3/1986 | Martin | 372/75 |
| 4,727,047 | 2/1988 | Bozler et al. | 437/89 |
| 4,769,680 | 9/1988 | Resor, III et al. | 355/43 |
| 4,774,205 | 9/1988 | Choi | 437/59 |
| 4,837,182 | 6/1989 | Bozler et al. | 437/966 |
| 4,846,931 | 7/1989 | Gmitter et al. | 156/633 |
| 4,855,255 | 8/1989 | Goodhue | 156/633 |
| 4,863,877 | 9/1989 | Fan et al. | 437/22 |
| 4,870,475 | 9/1989 | Endo et al. | 357/71 |
| 4,871,517 | 10/1989 | Falckenberg et al. | 156/DIG. 88 |
| 4,883,561 | 11/1989 | Gmitter et al. | 156/633 |
| 4,935,792 | 6/1990 | Tanaka et al. | 357/23.7 |
| 4,961,629 | 10/1990 | Kato | 350/332 |
| 4,979,002 | 12/1990 | Pankove | 357/17 |
| 5,045,895 | 9/1991 | Yoshida et al. | 357/17 |
| 5,073,806 | 12/1991 | Idei | 357/17 |

FOREIGN PATENT DOCUMENTS

| | | |
|---|---|---|
| 57-106181 | 7/1982 | Japan . |
| 61-280660 | 12/1986 | Japan 437/205 |
| 63-55529 | 3/1988 | Japan . |
| 64-38727 | 2/1989 | Japan . |
| WO90/09038 | 8/1990 | PCT Int'l Appl. . |
| WO91/02380 | 2/1991 | PCT Int'l Appl. . |

OTHER PUBLICATIONS

Milnes, E. G., "Semiconductor Heterojunction Topics: Introduction and Overview," *Solid-State Electronics* vol. 29, 2:99-121, (1986).

Akiyama, M. et al., "Growth of GaAs on Si and Its Application to FETs and LEDs," *Nat. Res. Soc. Symp. Proc.*, 67:53-64 (1986).

Turner, G. et al, "High-Speed Photoconductive Detectors Fabricated in Heteroepitaxial GaAs Layers," *Mat. Res. Soc. Symp. Proc.*, 67:181-188 (1986).

McDaniel, D. L. et al., "Vertical Cavity Surface-Emitting Semiconductor Laser with CW Injection Laser Pumping," *IEEE Photon Technol. Lett.*, Mar. 23, 1990.

Weber, J. P. et al., "Effects of Layer Thickness Variations on Vertical Cavity Surface-Emitting DBR Semiconductor Lasers", IEEE Photon Tech. Ltr., Mar. 23, 1990.

(List continued on next page.)

*Primary Examiner*—Olik Chaudhuri
*Assistant Examiner*—David E. Graybill
*Attorney, Agent, or Firm*—Hamilton, Brook, Smith & Reynolds

[57] ABSTRACT

The invention relates to the formation of arrays of thin film transistors (TFT's) on silicon substrates and the dicing and tiling of such substrates for transfer to a common module body.

16 Claims, 11 Drawing Sheets

OTHER PUBLICATIONS

"3-D Chip-On-Chip Stacking", *Semiconductor International*, Dec. 1991.

McClelland et al., "A Technique for Producing Epitaxial Films on Reusable Substrates", *Appl. Phys. Lett.* 37, 560, Sep. 15, 1980.

Yablonovitch et al., "Extreme Selectivity in the Lift-Off of Epitaxial GaAs Films", *Appl. Phys. Lett.* 51, 2222 Dec. 12, 1987.

Fan et al., "Lateral Epitaxy by Seeded Solidification for Growth of Crystal Si Films on Insulators", *Appl. Phys. Lett.*, 38, 365, Mar. 3, 1981.

Allen et al., "Characterization of Isolated Silicon Epitaxy Material", SPIE vol. 945—Advanced Processing of Semiconductor Devices II (Mar. 17–Mar. 18, 1988).

Conference Record of the 1991 International Display Research Conference, Oct. 15–17, 1991, IEEE.

Y. Hayashi et al., "A New Three Dimensional IC Fabrication Technology, Stacking Thin Film Dual-CMOS Layers" 1991 IEEE IEDM, pp. 657–660.

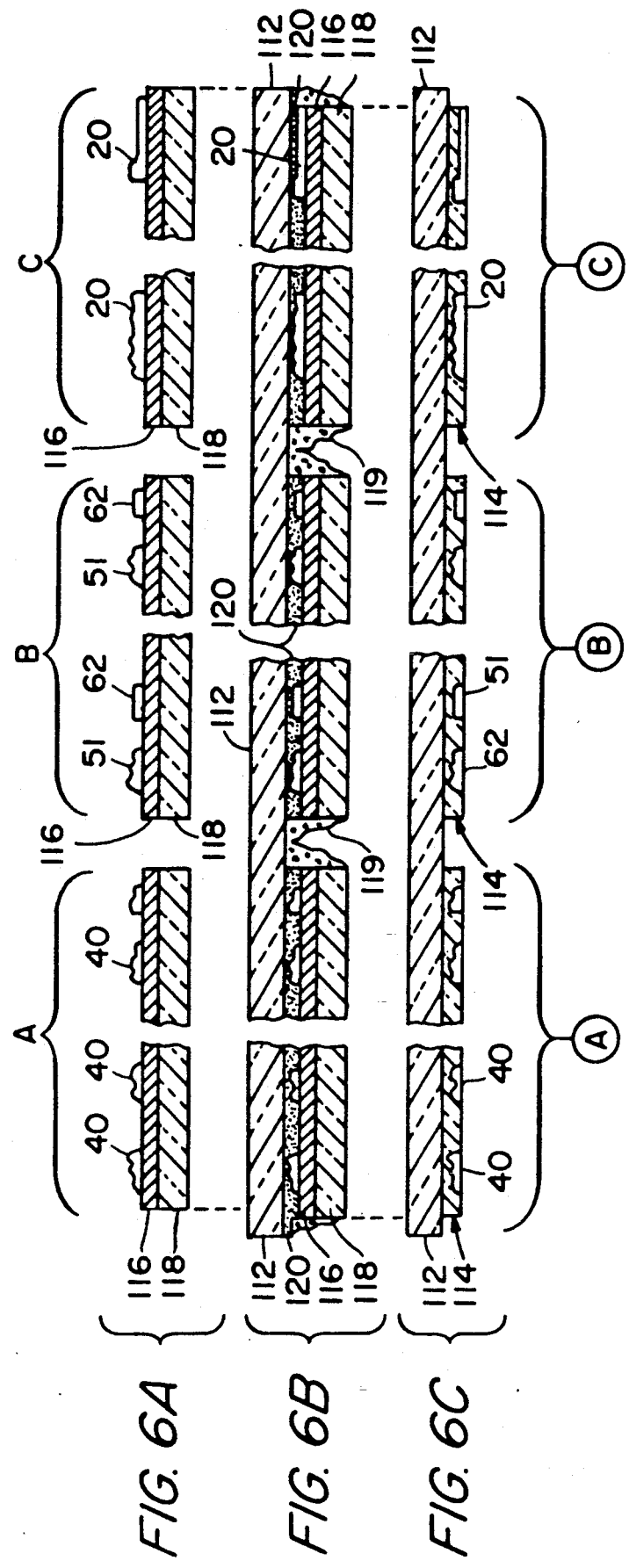

METHOD FOR MANUFACTURING A SEMICONDUCTOR DEVICE USING A CIRCUIT TRANSFER FILM

RELATED APPLICATIONS

This application is a continuation-in-part of U.S. Ser. No. 07/874,588 filed Apr. 24, 1992 entitled "High Density Electronic Circuit Modules" which is a continuation-in-part of U.S. Ser. No. 07/834,849 filed Feb. 13, 1992 entitled "High Density Electronic Circuit Modules" which is a continuation-in-part of U.S. Ser. No. 07/636,602 filed Dec. 31, 1990 entitled "Single Crystal Silicon Arrayed Devices for Display Panels", now U.S. Pat. No. 5,206,749, and a continuation-in-part of U.S. Ser. No. 07/643,552 filed Jan. 18, 1991 for "Light Emitting Diode Bars and Arrays and Method of Making Same" all of which are incorporated herein by reference.

BACKGROUND OF THE INVENTION

The development of new portable electronic products, such as the laptop computer, is currently of great worldwide interest. Miniaturization of the various component systems (memories, displays, and so forth) for such products requires that the necessary circuits be packed in as small a volume as possible. Packing circuits into a small volume also reduces parasitic capacitance and improves signal propagation time between circuits. One approach to this requirement is to increase the scale of integration in order to obtain all of the required functions from a circuit made from a single wafer. Unfortunately, efforts to create full-wafer circuitry have encountered unacceptable yield losses owing to the large circuit size. In the specific area of active matrix displays, a similar problem results in attempting the scale-up of the display size to and beyond the 256K pixel level.

Active matrix (AM) displays generally consist of flat-panels consisting of liquid crystals or electroluminescent materials which are switched "on" and "off" by electric fields emanating from pixel electrodes charged by thin film transistors (TFT's) co-located with each pixel electrode. These AM displays are expected to supplant cathode ray tube (CRT) technology and provide a more highly defined television picture or data display. The primary advantage of the active matrix approach, using TFT's, is the elimination of cross-talk between pixels, and the excellent grey scale that can be attained with TFT-compatible liquid crystal displays (LCD's).

Flat panel displays employing LCD's include a plurality of different layers: a first polarizing filter layer that is mounted on one side of a circuit panel on which the TFT's are arrayed to form pixels, a counter electrode layer and a filter layer containing at least three primary colors. A volume between the circuit panel and the filter plate is filled with a liquid crystal material. This material rotates the polarization of light passing through it when an appropriate electric field is applied across it. Thus, when a particular pixel electrode of the display is charged up by an associated TFT, the liquid crystal material rotates polarized light being transmitted through the material so that it will pass through the polarizing filter and be seen by the viewer.

The primary approach to TFT formation over the large areas required for flat panel displays has involved the use of films of amorphous silicon which has previously been developed for large-area photovoltaic devices. Although the TFT approach has proven to be feasible, the use of amorphous silicon compromises certain aspects of the panel performance. For example, amorphous silicon TFT's lack the frequency response needed for large area displays due to the low electron mobility inherent in amorphous material. Thus, the use of amorphous silicon limits display speed, and is also unsuitable for the fast logic needed to drive the display.

Owing to the limitations of amorphous silicon, other alternative materials are being considered, such as, polycrystalline silicon, or laser recrystallized silicon. Thin films, less than about 0.4 microns, of these materials are usually formed on glass which generally restricts further circuit processing to low temperatures.

The formation of large active-matrix displays is hampered by the unavailability of large-area single crystal Si (x-Si) material. Thus the conventional approach is to use thin film amorphous ($\alpha$-Si) or polycrystalline Si (poly-Si) wafers. The required number of thin film transistors (TFT's), combined with the large number of driver circuits and the thin film material defects inherent in $\alpha$-Si or poly-Si, leads to unacceptable yield and quality problems when the entire display is to be fabricated as a unit.

A need exists, therefore, for a relatively inexpensive way to reliably form hybrid high density electronic circuits, including active matrices, memories, and other devices, in a modular approach that permits small high-quality parts or circuits to be assembled into complete large-area high-quality complex devices.

SUMMARY OF THE INVENTION

The present invention comprises a method, and resulting apparatus, for fabricating AM displays, by using silicon thin film transfer processes to remove areas or tiles of circuits, formed in Si thin films, and transferring, locating and adhering the removed tiles to a common module body. The removal of areas or tiles is hereinafter referred to, generally, as "dicing." The process of transferring, locating and adhering is generally referred to as "tiling."

The films may be formed of $\alpha$-Si, poly-Si, or x-Si depending upon the desired circuit parameters. Elements of one circuit are then interconnected to elements of another circuit by conventional photolithographically patterned thin film metallization techniques. Direct laser writing or erasing may be used for repair or modification of interconnects.

The transfer may be accomplished in either of two ways — single transfer or double transfer. In the single transfer process, the desired Si circuitry is formed on a thin film Si substrate; the Si circuits are diced, i.e., divided into dice or tiles containing one or more circuits; the dice or tiles are then tiled, i.e., sequentially registered onto a common module body and sequentially adhered to the module body. After all the dice or tiles are adhered, all the Si substrates are removed in one process and the circuits interconnected.

In the double transfer process, the circuits are transferred to an intermediary transfer or carrier body and then the substrates are removed. Dicing may occur before or after the first transferral. The thin film circuitry is supported by the transfer body until transfer to the common module body is appropriate. The circuitry is then tiled, i.e., sequentially transferred, registered and adhered to the common module body. If the transfer body is sufficiently thin, the transfer body may be left on the circuitry. If not, it is removed and circuit interconnections made, as required.

In a preferred embodiment, the common module forms an active matrix (AM) LCD panel fabricated in accordance with the invention. The circuit panel for the AMLCD is formed by transferring to a common module substrate or superstrate, multiple x-Si and/or a-Si or poly-Si thin film tiles upon which circuits may have been formed, and wherein each tile is obtained as a unit from one or more wafers. During transfer, the tiles are registered with respect to one another. Circuits are then interconnected as necessary. Registration is accomplished by well-known X-Y micropositioning equipment. Adherence and planarity are achieved using optically transparent adhesives which fill in voids left in forming circuitry. Trimming of substrate edges may be required to obtain precise circuit dimensions needed for proper alignment on the module body.

BRIEF DESCRIPTION OF THE DRAWINGS

FIGS. 6A–6D is a process flow sequence illustrating a single transfer process and bonding of tiles of a silicon on oxide (SOI) circuit structure to a common module.

DETAILED DESCRIPTION OF THE INVENTION

I. Tiled Active Matrix Liquid Crystal Display

Figure 1:
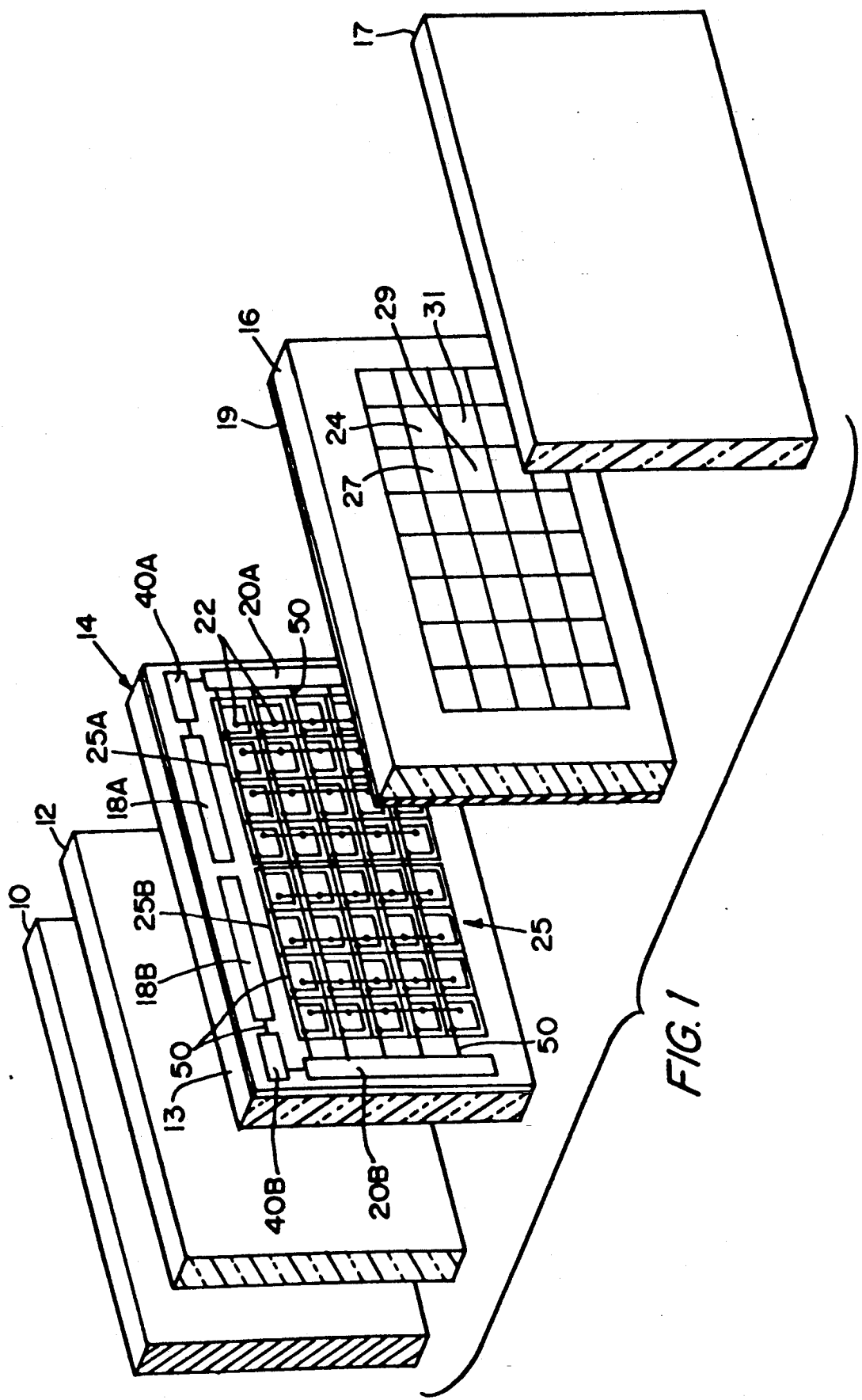
FIG. 1 is a perspective view of a high density circuit module in the form of an active matrix liquid circuit display (AMLCD).

A preferred embodiment of the invention for fabricating complex hybrid multi-function circuitry on common module substrates is illustrated in the context of an AMLCD, as shown in FIG. 1. The basic components of the AMLCD comprise a light source 10, such as a flat fluorescent or incandescent white lamp, or an electroluminescent lamp having white, or red, blue and green phosphors, a first polarizing filter 12, a circuit panel 14, an optional filter plate 16 and a second polarizing filter 17, which form a layered structure. Note: Filter plate 16 is not needed for a black and white display or where the red, green and blue colors are provided by the lamp at the appropriate pixel. A liquid crystal material 19, such as a twisted nematic is placed between the circuit panel 14 and the filter plate 16.

Figure 2A:
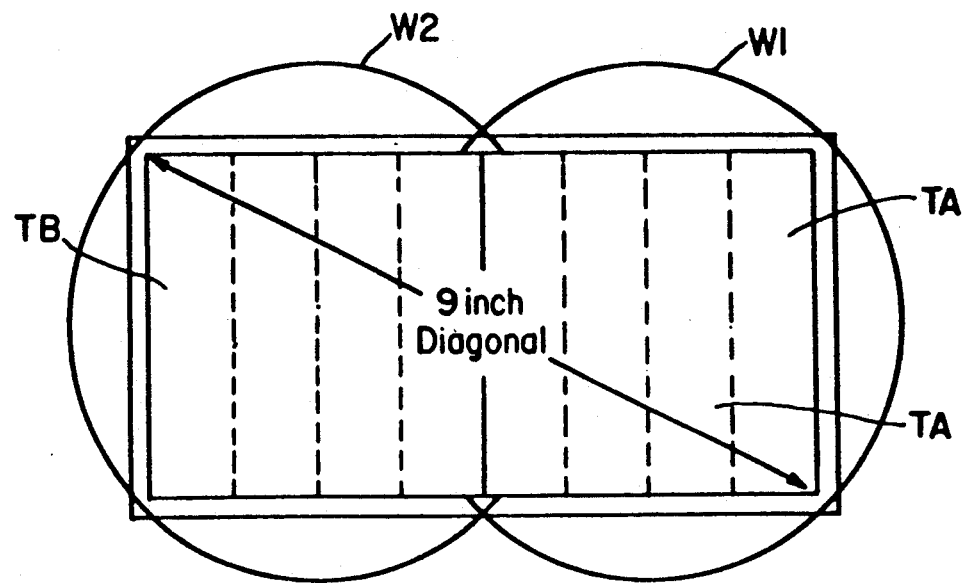
FIG. 2A is a schematic illustrating how two six inch wafers can be used to form tiles for a 4×8 inch AMLCD.
Figure 2B:
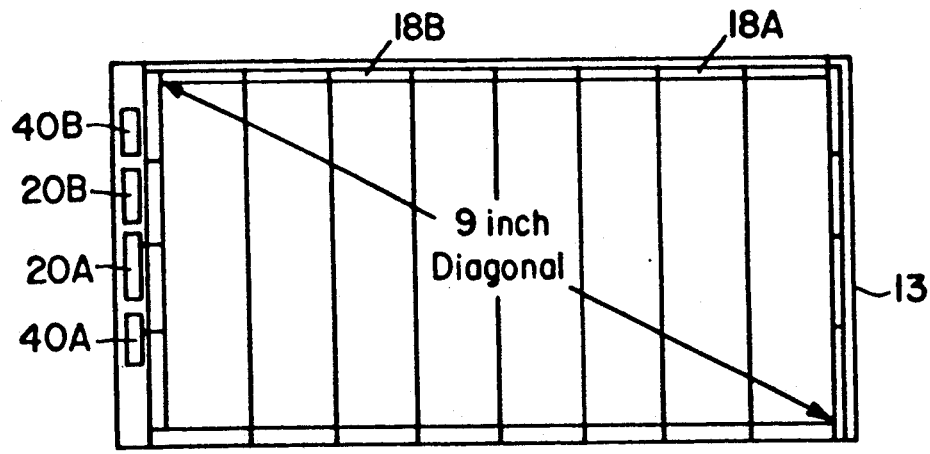
FIG. 2B shows the tiles of FIG. 2A applied to a glass substrate for forming an AMLCD.

Circuit panel 14 consists of a transparent common module body 13 formed, for example, of glass upon which is transferred a plurality of common multifunction circuits comprising control logic circuits 40A and 40B and drive circuits 18A and 18B, 20A and 20B, and array circuits 25A and 25B. Preferably, the logic and drive circuits which require high speed operation are formed in tiles of x-Si. The array circuits may be formed in a-Si material, or poly-Si, or preferably in x-Si, to achieve lower leakage in the resultant TFT's and, hence, better grey scale. Higher speed is also achieved in x-Si. A 4×8 inch active matrix LCD array can be formed from two standard 6-inch diameter Si wafers W1 and W2 as shown in FIG. 2A. Array circuit 25A is formed on wafer W1 and 1-inch by 4-inch tiles TA are transferred from the wafer W1 to the substrate 14. Note: The transfer may be accomplished using either a single or double transfer process, as will be described in detail below. Each tile is registered against another using micropositioning equipment and manipulators capable of micron scale accuracy. Similarly, tiles TB are transferred from wafer W2 to form array 25B on substrate or common module body 13 (See FIG. 2B).

Logic circuits 40A and 40B and drive circuits 18A, 18B, 20A, 20B are formed on other suitable substrates (not shown) and tiled and transferred in like manner to common substrate 13 and registered opposite the arrays 25A, 25B, as shown in FIG. 1. Conductive interconnections 50 are then made between the drive circuits and the individual pixels 22 and the logic control circuits 40A and 40B. In this manner, a 1280 by 1024 addressable array of pixels 22 are formed on the substrate 13 of circuit panel 14. Each pixel 22 is comprised of TFT actuated by voltage from a respective drive circuit 18A or B on the X-axis and 20A or B on the Y-axis and an associated pixel electrode (not shown). The X and Y drive circuits are controlled by signals from control logic circuits 40A and B. Each pixel 22 produces an electric field across the liquid crystal material 23 disposed between the pixel and a counterelectrode (not shown) formed on the back side of the color filter plate 16.

The electric field formed by pixels 22 causes a rotation of the polarization of light being transmitted across the liquid crystal material that results in an adjacent color filter element being illuminated. The color filters of filter plate system 16 are arranged into groups of four filter elements, such as blue 24, green 31, red 27, and white 29. The pixels associated with filter elements can be selectively actuated to provide any desired color for that pixel group.

Figure 3:
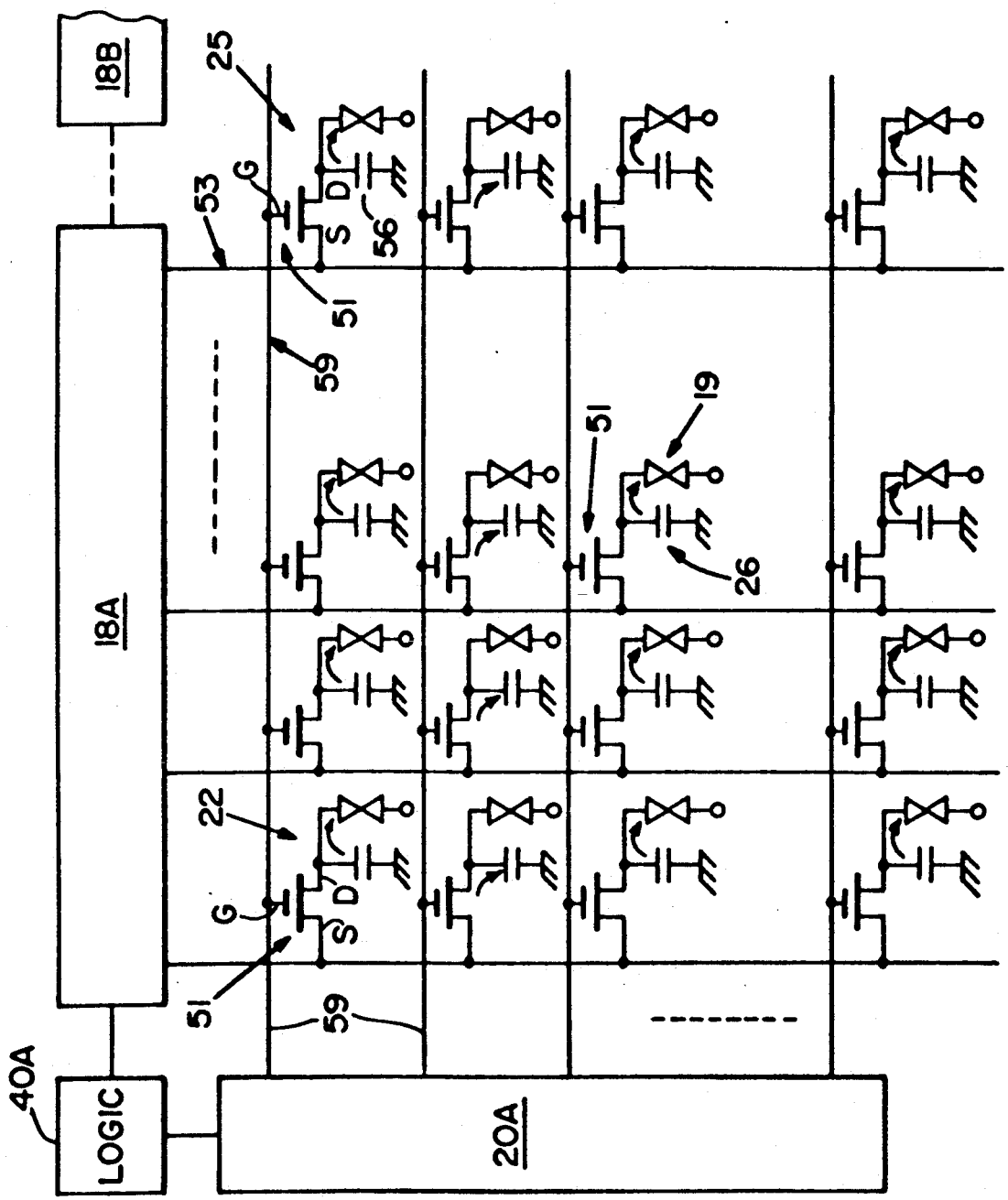
FIG. 3 is a circuit diagram illustrating the driver system for the AMLCD of FIG. 1.

A typical drive and logic circuit that can be used to control the array pixels 22 is illustrated in FIG. 3. Drive circuit 18A receives an incoming signal from control logic 40A and sends a signal to each source electrode of a TFT 51 in one of the columns selected by logic circuit 40A through interconnect line 53. Y-drive circuit 20A controlled by logic circuit 40A energizes a row buss 59 extending perpendicular to column buss 53 and applies a voltage pulse to each gate G of TFT's 51 in a selected row. When a TFT has a voltage pulse on both its gate and source electrode current flows through an individual transistor 51, which charges capacitor 56 in a respective pixel 22. The capacitor 56 sustains a charge on the pixel electrode adjacent to the liquid crystal material (shown schematically at 19) until the next scan of the pixel array 25. Note: The various embodiments of the invention may, or may not, utilize capacitors 56 with each pixel depending upon the type of display desired.

II. Transfer Processes

The array circuits 25A and 25B and logic 40A, 40B and drive circuits 18A, 18B may be formed and transferred by a number of processes. The basic steps in a single transfer process are: forming of a plurality of thin film Si circuits on Si substrates, dicing the thin film to form tiles, and transferring the tiles to a common module substrate by "tiling." Tiling involves the steps of transferring, registering the transferred tiles, and adhering the registered tiles. The Si substrates are then removed and the circuits on the tiles are interconnected.

Formation of the thin film circuits is described in detail below in connection with FIGS. 4A–4H. The thin film circuits are transferred to an intermediate transfer body or carrier 80 (FIG. 5A) and then diced and transferred to the common module body (a so-called double transfer) for further processing (FIGS. 5A–5D).

Figure 4A:
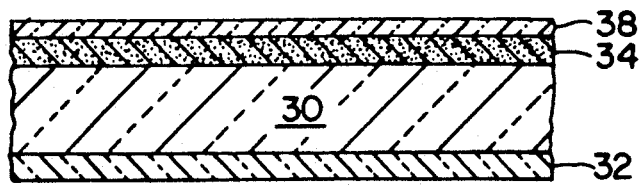
FIGS. 4A–4H is a preferred process flow sequence illustrating the fabrication of a tile for the circuit panel for the AMLCD of FIG. 1.

A silicon-on-insulator (SOI) structure, such as that shown in FIG. 4A, is formed using well-known techniques. The SOI structure consists of a substrate 30 of x-Si, and an insulator layer 34 (such as, for example, $SiO_2$) and a thin essentially single crystal layer 38 of silicon formed over the insulator layer 34. The insulator 34 is thus buried beneath the Si surface layer.

Note: for the purposes of the present application, the term "essentially" single crystal means a film in which a majority of crystals show a common crystalline orientation and extend over a cross-sectional area in a plane of the film for at least 0.1 $cm^2$, and preferably, in the range of 0.5–1.0 $cm^2$, or more. The term also includes completely single crystal Si.

The use of a buried insulator provides devices having higher speeds than can be obtained in conventional bulk (Czochralski) material. An optional capping layer (not shown) also of silicon nitride may also be formed over layer 36 and removed when active devices are formed.

Figure 4B:
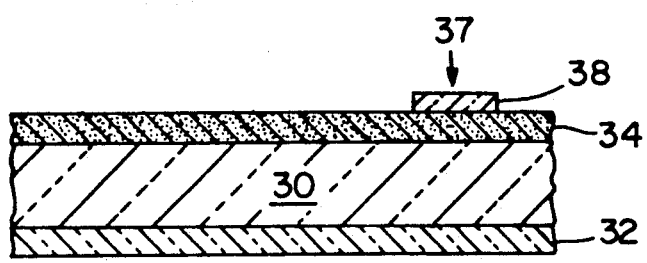
Figure 4C:
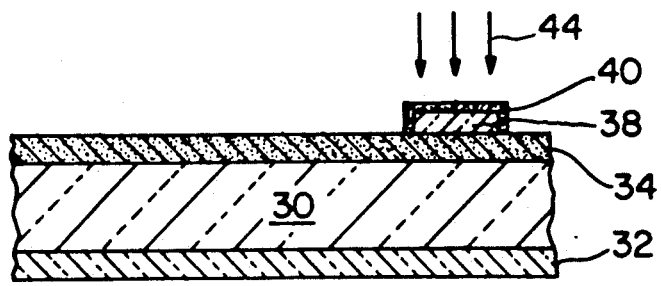
Figure 4D:
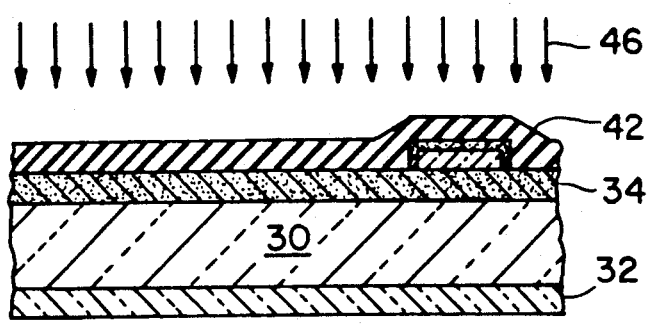

As shown in FIG. 4B, the film 38 is patterned to define active circuits, such as a TFT's in region 37. Note: For simplification, only one TFT 51 (FIG. 4G) and one pixel electrode 62 will be illustrated (FIG. 5D). It should be understood that an array of 1280 by 1024 such elements can in practice be formed on a single 6-inch wafer.

A plurality of arrays may be formed on a single six-inch wafer, which are then applied to the display as tiles and interconnected. Alternatively, the plurality of pixel matrices from one wafer can be separated and used in different displays. The plurality may comprise one large rectangular array surrounded by several smaller arrays (to be used in smaller displays). By mixing rectangular arrays of different areas, such an arrangement makes better use of the total available area on a round wafer.

An oxide layer 40 is then formed over the patterned region 38 where the TFT's are to be located. The intrinsic crystallized material 38 is then implanted 44 (see arrows at FIG. 4C) with phosphorous or other n-type dopants to provide a p-channel device (or alternatively, a p-type dopant for an n-channel device).

Figure 4E:
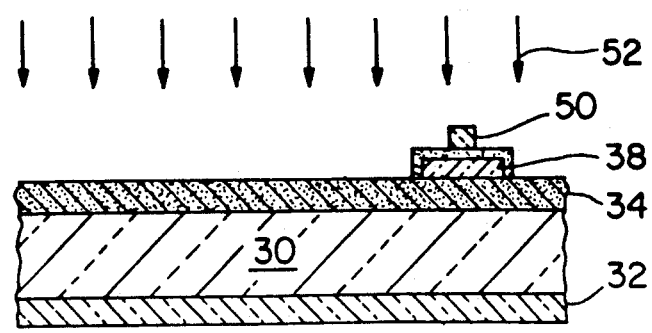
Figure 4F:
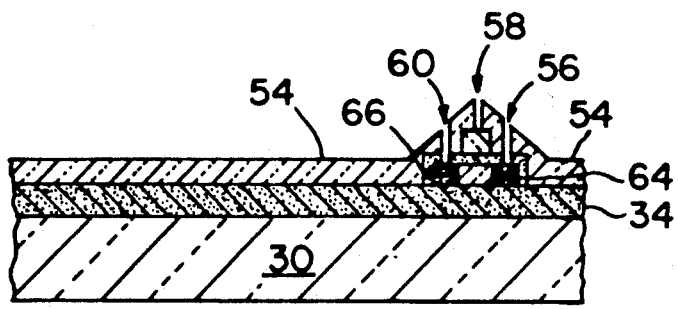
Figure 4G:
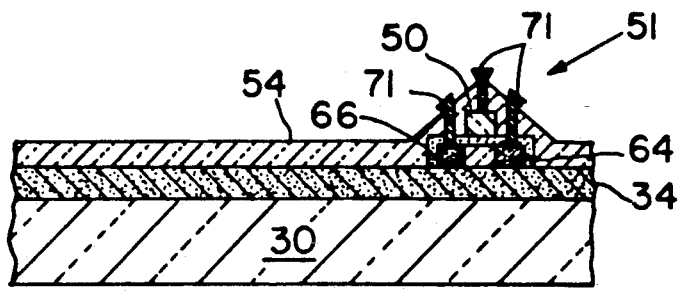

A polycrystalline silicon layer 42 is then deposited over layers 40 and 34 and layer 42 is then implanted (see arrows 46 in FIG. 4D) with an n-type dopant to lower the resistivity of the layer 42 to be used as the gate 50 of the TFT. Next, the implanted polysilicon 42 is patterned to form the gate 50, as seen in FIG. 4E, followed by a large implant 52 of boron to provide p+ source and drain regions 66, 64 for the TFT on either side of the gate electrode (as shown in FIG. 4F). An oxide 54 is then formed over the device and openings 60, 56, 58 are formed through the oxide 54 to provide contact vias to the source 66, the drain 64, and the gate 50. A patterned metallization 71 of aluminum, tungsten or other suitable metal is used to provide metal contacts to the TFT 51 (FIG. 4G). Driver circuits in the form of CMOS devices may also be formed along with the TFT's using well-known process techniques.

Figure 4H:
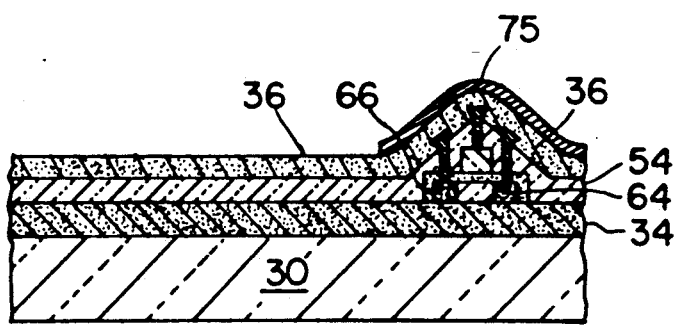

Next, a protective layer 36 of nitride or oxynitride is formed over the structure (FIG. 4H). Layer 36 also may act as an etch stop for further processing. A light shield 75 of opaque material, such as aluminum, is then deposited through a mask to shield the top of TFT 51 from light rays which would otherwise deteriorate transistor performance.

The TFT devices have now been processed and may now be tested and repaired, as required, before further processing occurs.

The next steps in the process is to transfer the silicon TFT circuit film to a common module, either directly, or by a double transfer, i.e., from substrate to carrier and then to the common module. Preferably, the process may include formation of a bottom light shield for the TFT's, formation of the pixel electrodes and the interconnection, as will be described in connection with FIGS. 5A–5D.

Figure 5A:
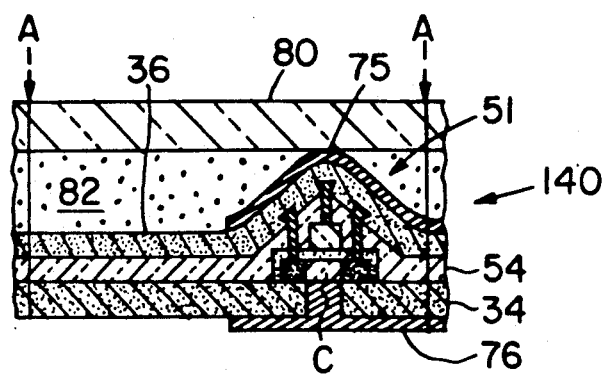
FIGS. 5A through 5E are cross-sectional schematic process views of formation of the AMLCD using a double transfer process.

In the double transfer approach, an epoxy 82 is used to attach a temporary intermediate carrier, or superstrate 80, to the circuit film 140 (FIG. 5A). A bottom shield 76 is then formed beneath TFT 51. Optionally, shield 76 may be used to contact body B of TFT, so as to provide a ground contact and minimize stray capacitance. To do this, an opening is formed beneath the TFT 51 and metallization is deposited, as shown in FIG. 5A.

Note that at this point, the pixel electrodes have not been formed. This step in the process has been delayed until the tiles are transferred to the common module body 110, so that all the electrodes will be made at the same time and the pixel periodicity will be constant over the display panel and unaffected by any registration placement errors.

Figure 5B:
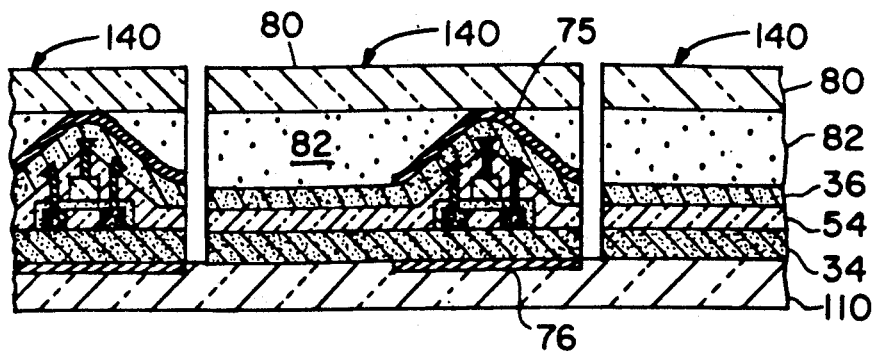

As shown in FIG. 5B, a plurality of tile structures 140 are then sequentially registered with one another and adhered to a common module body 110 using a suitable adhesive (not shown). Common module body 110 is preferably patterned with registration marks and interconnect metallization on the surface facing the tile structure 140 for interconnecting individual tile circuitry with each other. Next, insulation and alignment layers, spacers, a sealing border and bonding pads for connections (not shown) are formed on the periphery of the common module body 110. A screen printing process can be used to prepare the border.

Figure 5C:
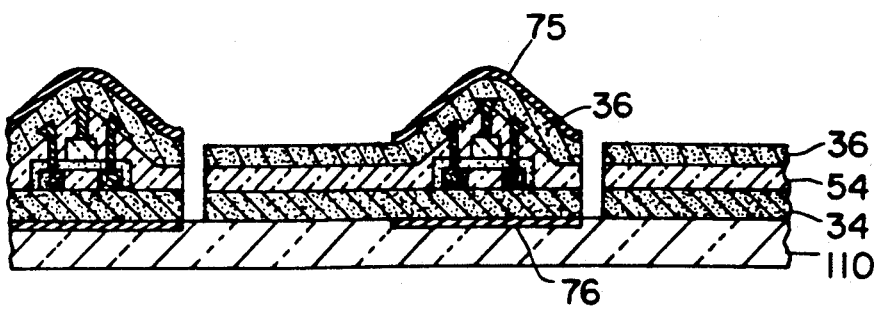
Figure 5D:
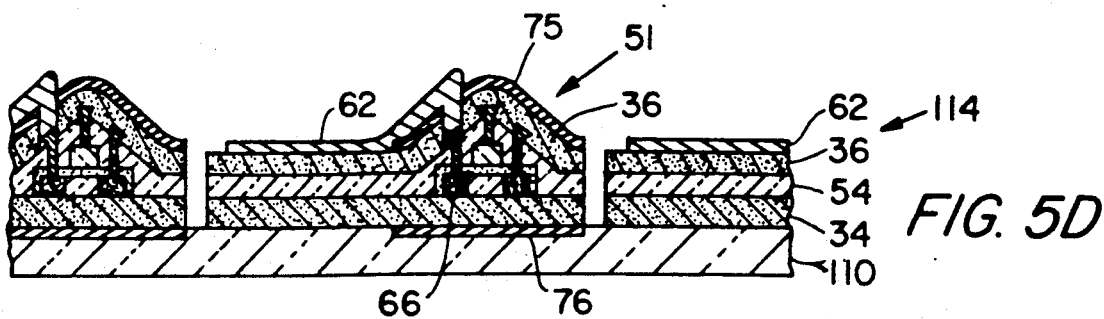

After all the circuit tiles are registered and adhered to the module body 110, the transfer body 80 and the epoxy 82 are removed using a suitable etchant. The acid HF is suitable for a glass transfer body secured by a cycloaliphatic anhydride adhesive (FIG. 5C). In this case, the edges of the tiles should be protected with silicon nitride or other substance impervious to the etchant in order to protect the tile edges from attack. After the transfer body 80 is etched off, the epoxy 82 is removed by oxygen plasma, sulfuric acid or boiling trichloroethylene. Alternately, a removable epoxy can be used. In this case, the module body is exposed to heat, UV radiation, microwave radiation or chemicals to diminish or remove the adhesive properties of the selected adhesive 82, allowing the glass 80 to be lifted off. Any residual epoxy could be removed in one of the above-mentioned ways.

At this point in the process, the pixel electrodes 62 are formed and connected to the source terminal 66 of the TFT's 51 by depositing transparent electrical conductor, such as Indium Tin Oxide (ITO), over the protective coating 36 and into vias formed at the TFT source terminal 66. The structure shown in FIG. 5D is now ready to be combined with other elements of a liquid crystal display to form a complete panel.

Figure 5E:
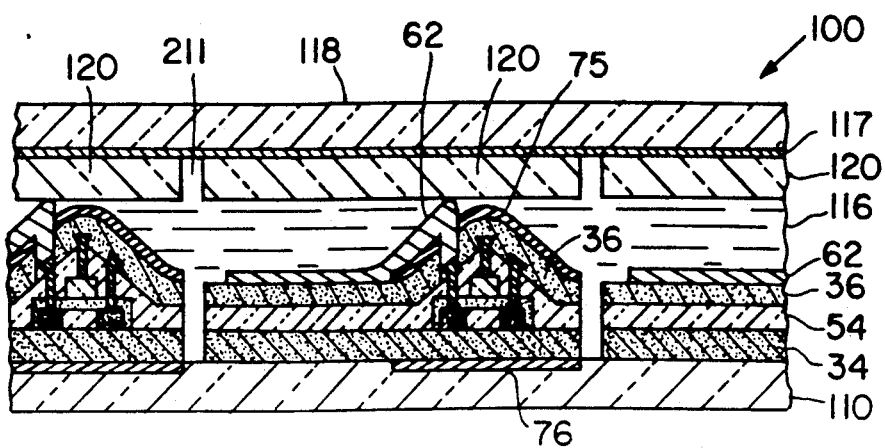

As shown in FIG. 5E, a polarizer 118, a counterelectrode plate 117 and color filters 120 are bonded to the periphery of the FIG. 5D tile structure 114 with the sealing border after insertion of spacers (not shown). The display is filled with the selected liquid crystal material 116 via small filling holes (not shown) extending through the border. The filling holes are then sealed with a resin or epoxy.

Pixel electrodes 62 are laterally spaced from each other. Each pixel has a transistor 51 and a color filter 120 associated therewith.

III. Alternate Adhesion and Transfer Processes

Figure 6D:
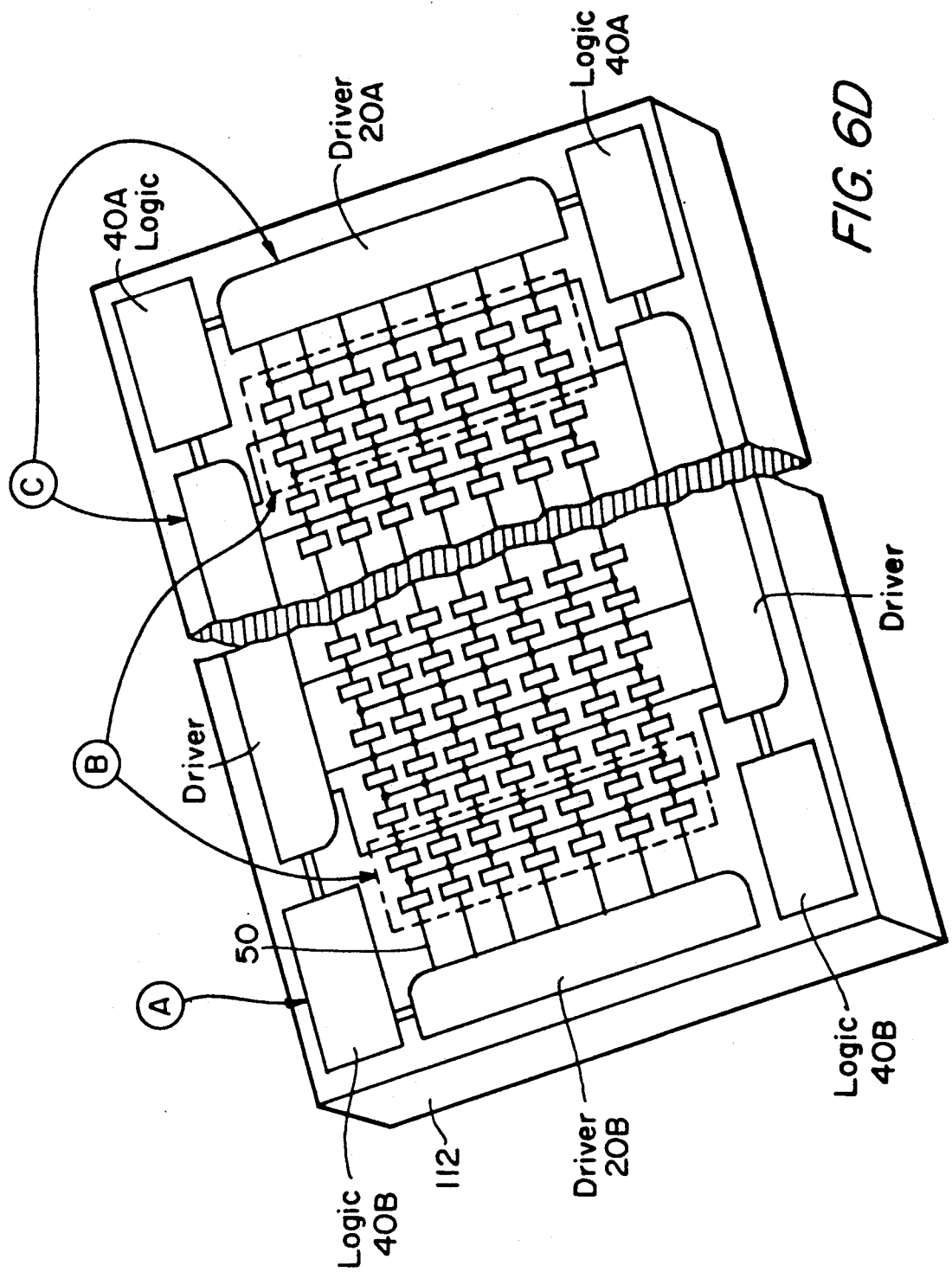

FIGS. 6A and 6D illustrate an alternate preferred single transfer process for adhering and transferring tiles of circuits of thin films of silicon to a common module body. The starting structure is a silicon wafer 118 upon which an oxide layer 116 and a thin film of poly-Si, α-Si or x-Si 114 is formed using any of the described processes such as ISE or CLEFT. A plurality of circuits, such as TFT's, Si drivers and Si logic circuits, are then formed in the thin film. FIG. 6A shows three such wafers, A, B, C. In wafer A, logic circuits 40 are formed. In wafer B, TFT's 51 are formed. In wafer C, driver circuits 20 are formed. The wafers are diced into tiles which are exactly defined using dicing saw, laser scribe, water jet, backlapping and photolithographically defined etched edges taking advantage of the anistropy of some silicon etchants. A wafer, or individual tiles diced from the wafer, is attached to a common module body 112, such as glass or other transparent insulator, using an adhesive 120 that meets the general requirements described below:

General Adhesive Requirements

Preferably the adhesive is comprised of an epoxy, such as, a cycloaliphatic anhydride; for example, EP-112 made by Masterbond Inc. The adhesive must satisfy the following criteria:
  Excellent spectral transmission in the visible range;
  Good adhesion to glass, oxides, metals, nitrides;
  No reactions with glass, metals, oxides, nitrides;
  Low shrinkage;
  Low warp/stress;
  Able to tolerate acids at 100° C. for extended periods without lifting, losing adhesion, or degrading;
  Able to withstand 180° C. for 2 hours with no optical change;
  Good resistance to acids and solvents;
  Able to tolerate dicing and heating steps (including an acid etch step with no lifting);
  Low viscosity to allow thin adhesive films; and
  Ability to be vacuum degassed to eliminate all bubbles.

In general, the cycloaliphatic anhydrides meet most of the above criteria. The epoxy preferably has a low cure temperature to minimize shrinkage, a very low ion content (<5 ppm) and spectral stability over extended time periods.

Multiple tiles are registered in X,Y, and Z axis using well-known XY positioning techniques combined with Z axis positioning. X,Y positioning can be achieved using registration marks prefabricated on the common module body 112. The Z axis positioning can be accomplished using vacuum chucks and accurate, reproducible pressure to hold the tiles flat during positioning and adhesive tacking. Alternately, optically assisted Z registration could be used to guarantee that the critical tile edges are at exactly the same height when tacked in place.

After the tiles A,B,C are attached, using the adhesive 120, to the common module body 112, the adhesive is vacuum degassed to eliminate all bubbles. The sandwich structure is then cured at a low temperature of about 100° to 130° for 4–8 hours which causes the adhesive to gel and minimizes the shrinkage characteristics. Then the adhesive is fully cured at a higher temperature of about 160° C. for about 8 hours. This cure assures that the bonds are fully matured. Without this cure, the adhesive will not stand up to the subsequent chemical etching step.

The wafer, or tile, is then cleaned and the edges protected with a bead of material 119, such as an adhesive, or spin on glass, or polyamide, which etches at a rate equal to or slower than the substrate 118 (FIG. 6B). The wafer is put into a solution (KOH or equivalent) of 25 grams to 75 ml $H_2O$ at 100° C. Depending on the thickness of the wafer, it may take up to 5 hours to etch the Si 118 down to oxide layers 116. The solution etches silicon very rapidly, i.e. 2 to 3 microns/min., and uniformly. The acid has a very low etch rate on oxide, so that as the substrate is etched away and the buried oxide is exposed, the etching rate goes down. The selectivity of the silicon etch rate in KOH versus the oxide etch rate in KOH is very high (200:1). This selectivity, combined with the uniformity of the silicon etching, allows the observer to monitor the process and to stop the etch in the buried oxide layer 116 without punching through to the thin silicon layer 114 above it. Wafers up to 25 mils thick and oxides as thin as 4000 Å have been successfully etched using this process. An alternative etchant is hydrazine, which has a much higher etch rate selectivity or ethylene diamine pyrocatacol (EDP).

When the silicon is completely gone, the vigorous bubbling, which is characteristic of silicon etching in KOH, abruptly stops, signalling that the etching is complete.

Finally, if necessary, the edge protection material is removed using, for instance, oxygen plasma. Interconnection of tiles and backside processing are now done on the back side to complete the module.

Alternate Embodiment

An alternate one-step transfer process will now be described in connection with FIGS. 7A–7H wherein like items in FIGS. 4A–4H carry the same numeral with a prime suffix. This process begins as in FIG. 4G, except that after oxide 54' is formed, an additional opening 37 is formed through the oxide 54 to provide an additional contact for a pixel electrode to be added later. A patterned metallization 71' of aluminum, tungsten or other suitable conductor is used to provide metal contacts to the TFT 51 and to form contact pad 39 on insulator 34'. An interconnect lead 35 can be deposited connecting source region 66' to pad 39.

Figure 7A:
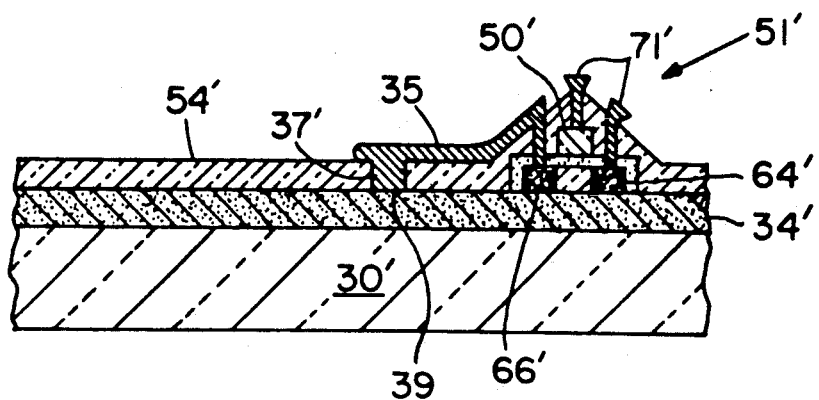
FIGS. 7A–7H is a process flow sequence illustrating an alternative single transfer process of the invention.
Figure 7B:
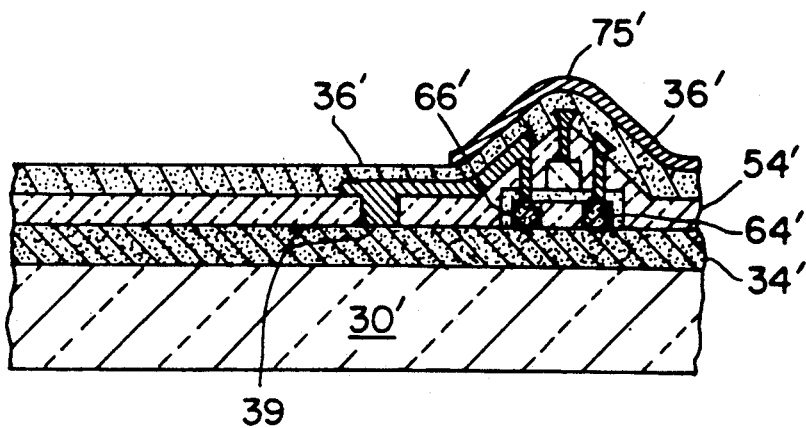

Next, a protective layer 36' of nitride or oxynitride is formed over the structure (FIG. 7B). A light shield 75' of opaque material is then deposited through a mask to shield the top of TFT 51 from light rays.

Figure 7C:
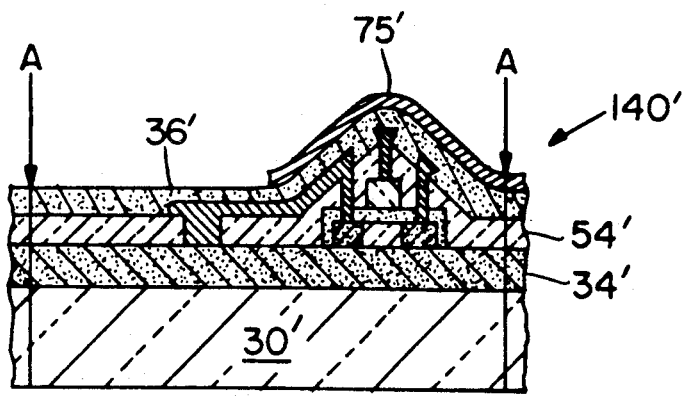
Figure 7D:
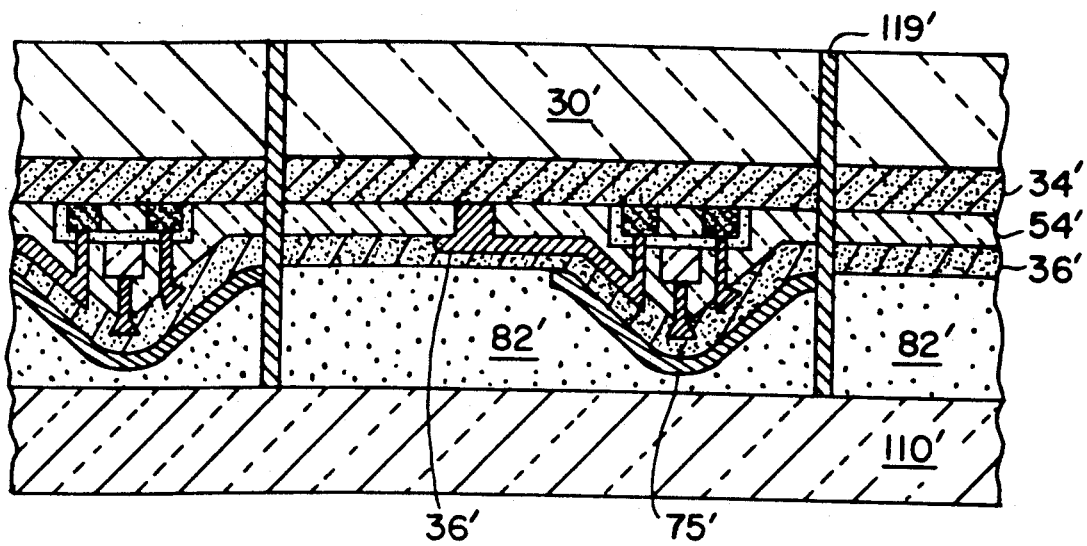
Figure 7E:
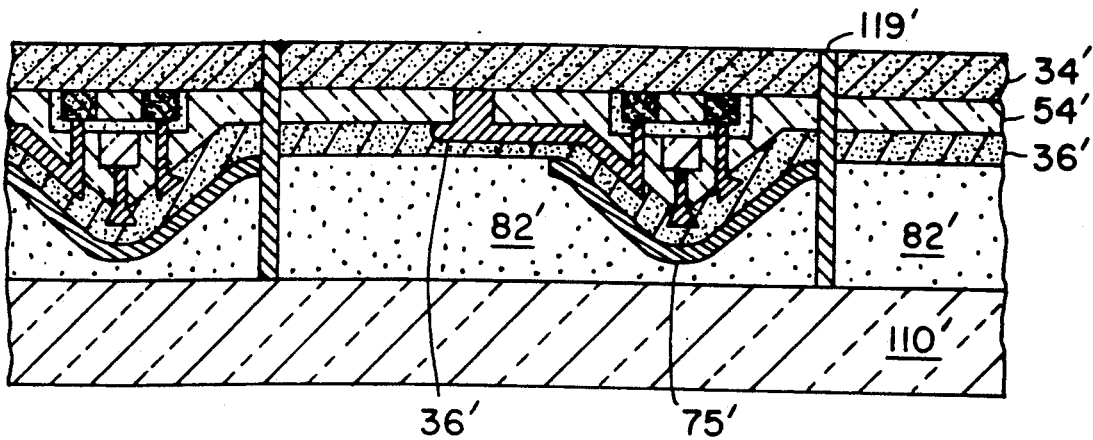

As shown in FIGS. 7C and 7D, a plurality of tile structures are formed by dicing the FIG. 7B structure along lines A—A. These tiles are then inverted, registered with one another, and adhered to a common module body 110' using a suitable epoxy adhesive 82'.

Figure 7F:
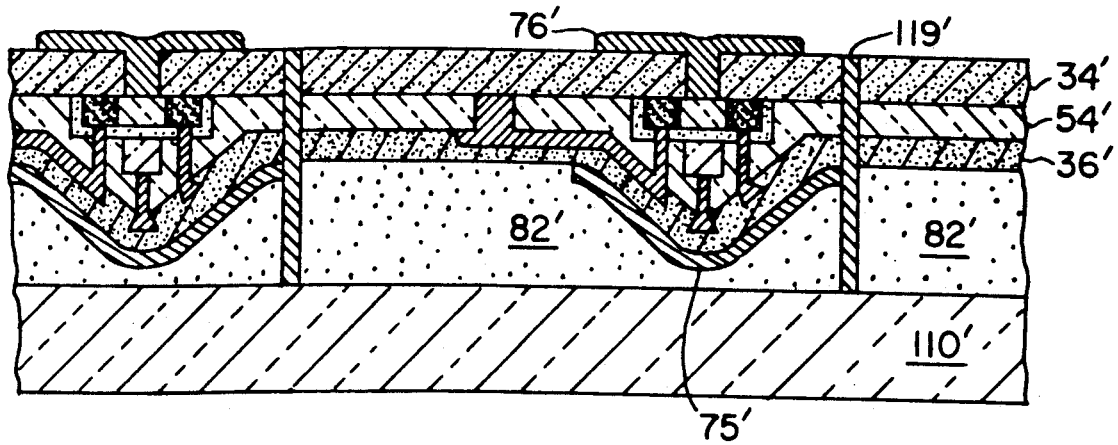

After all the circuit tiles are registered and adhered to the module body 110', the x-Si substrate 30' is removed by preferential etching down to the insulator 34'. The edges of the tiles are protected with silicon nitride 119' or other substance impervious to the etchant in order to protect the tile edges from attack. After the substrate is etched off (FIG. 7E), openings are made in the insulator 34' opposite the base region of TFT 51 and an opaque conductive shield 76' is selectively deposited over the TFT 51 to shield the TFT (FIG. 7F). This shield may also be grounded by interconnect metallization (not shown) to prevent undesired stray capacitance effects and undesired parasitic bipolar latchup, which would otherwise occur if the body of the TFT was left floating.

Figure 7G:
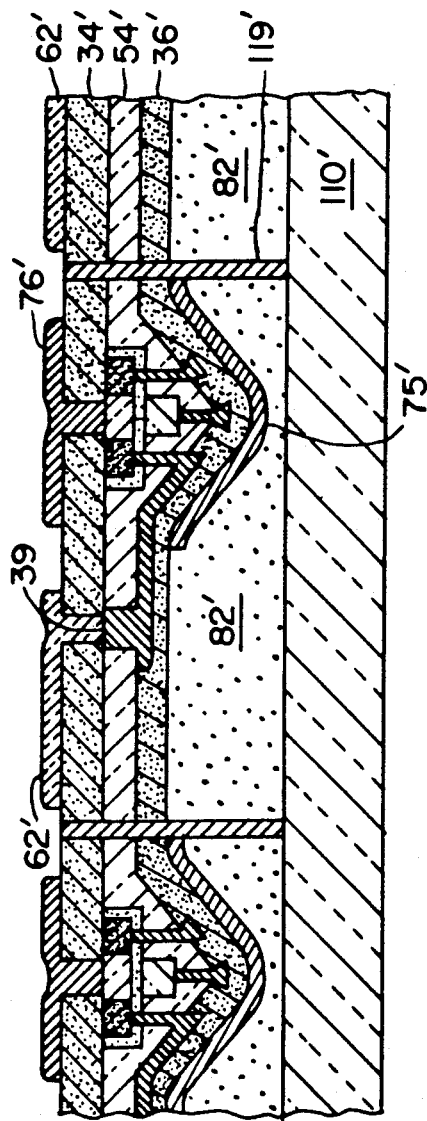

Next, the pixel electrodes 62' are formed in the insulator 34' opposite pad 39 (FIG. 7G) at the same time for all tiles, thereby providing a constant periodicity over the display panel. The structure shown in FIG. 7G is now ready to be combined with other elements of a liquid crystal display to form a complete panel.

A polarizer 118', a counterelectrode plate 117' and color filters 120' are bonded to the periphery of the tile structure (not shown). The display is filled with the selected liquid crystal material 116' via small filling holes (not shown) extending through the border.

Pixel electrodes 62' are laterally spaced from each other. Each pixel has a transistor 51' and a color filter 120' associated therewith.

Figure 7H:
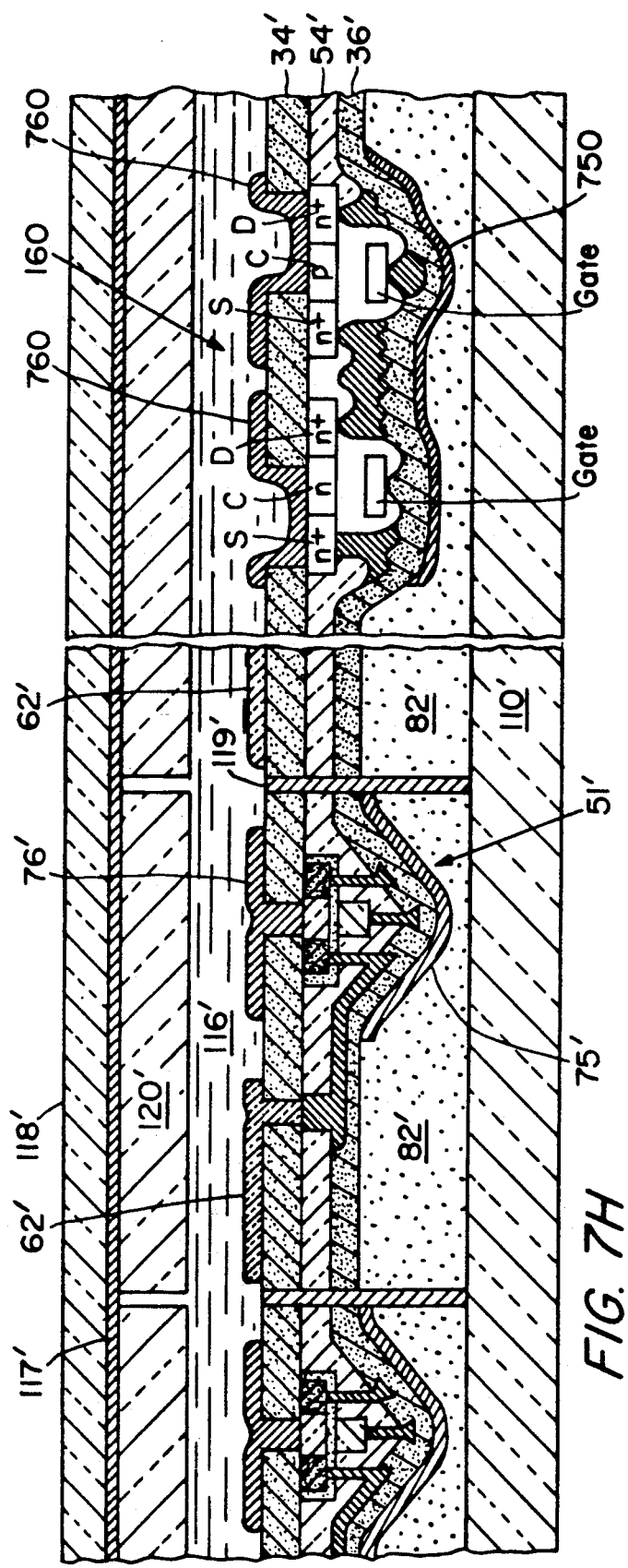

Also shown in FIG. 7H is a complementary metal oxide semiconductor (CMOS) driver which may be formed on the same wafer as was used to form the TFT tiles and/or may be formed on the same tile using the same layers 34', 54' and 36' and carrying the same light shielding metallization 750 and 760. Light shield 760 also serves to connect the source regions S to the body region B of each MOS device thereby eliminating uncontrolled floating body effects as previously mentioned.

The main advantages of the FIG. 7 embodiment are (i) the location of the pixel electrodes 62' in close proximity to the counterelectrode 117' to activate the liquid crystal material as compared to the conventional case in which the electrode is made of the same material as the TFT and located on the same side as the TFT; and (ii) the constant gap for the liquid crystal eliminates disclination effects.

Equivalents

While the invention has been particularly shown and described with reference to preferred embodiments thereof, it will be understood by those skilled in the art that various changes in form and details may be made therein without departing form the spirit and scope of the invention as defined by the appended claims.

We claim:

1. The process of forming electronic circuitry on a common body comprising the steps of:

a) forming a plurality of electronic circuits in a semiconductor film formed on a substrate;
   b) dividing the substrate into a plurality of tiles;
   c) transferring said tiles to a common body;
   d) registering the tiles on said common body;
   e) adhering said tiles to the common body;
   f) removing the substrates tiles, leaving the circuits on the body; and
   g) simultaneously forming circuit elements on said circuits so that each such element is aligned with each other element.

2. The process of claim 1 wherein the circuits are transistors and the elements are electrodes.

3. The process of claim 2 wherein the transistors are field effect transistors having source and drain regions extending in a plane and formed on opposite sides of a gate region and opaque shields formed on opposite sides of said plane.

4. The process of claim 1 wherein the circuits are formed in recrystallized polysilicon formed over a buried insulator and wherein the recrystallized polysilicon forms a essentially single crystal layer.

5. The process of claim 2 wherein the electrodes are formed of transparent conductive material.

6. The process of claim 3 including the step of covering transistors on two sides of the film by opaque material.

7. The process of claim 1 wherein the electronic circuits comprise thin film transistor circuits and driver circuits.

8. The process of claim 6 wherein the tiles are adhered using an ultra-violet light curing adhesive.

9. The process of claim 5 wherein the electrodes are formed of indium tin oxide.

10. The process of claim 7 wherein the tiles are divided using a process from the group comprising: sawing, cleaving or etching.

11. The process of forming transistors and pixel electrodes for an active matrix liquid display comprising the steps of:

a) forming a plurality of transistors in a first semiconductor film formed on a first substrate;
    b) dividing the substrate into circuit tiles and transferring said tiles to a common body;
    c) removing the substrates from the tiles leaving the transistors on the body;
    d) forming electrodes on the tiles adjacent the transistors.

12. The process of claim 11 wherein the film is formed of silicon material from the group comprising amorphous Si, polysilicon or single crystal silicon.

13. The process of claim 11 wherein the electrodes are formed of indium tin oxide.

14. The process of claim 11 wherein the transistors are covered by opaque material on sides opposite the plane of the film.

15. The process of claim 11 including an intermediate step in which the tiles are transferred to a transfer body where the substrates are removed before transfer of the tiles to the common body.

16. The process of claim 14 wherein the transistors have source, drain and body regions and wherein the opaque material is electrically conductive and is used to contact one or more of said regions to minimize stray capacitance effects.

* * * * *

UNITED STATES PATENT AND TRADEMARK OFFICE
CERTIFICATE OF CORRECTION

PATENT NO. : 5,256,562
DATED : October 26, 1993
INVENTOR(S) : Duy-Phach Vu, Brenda D. Dingle, Jason E. Dingle and Ngwe Cheong It is certified that error appears in the above-indentified patent and that said Letters Patent is hereby corrected as shown below:

Claim 1, at column 10, line 7, after "substrates" insert ---from the---.

Signed and Sealed this

Twenty-fifth Day of October, 1994

Attest:

BRUCE LEHMAN

Attesting Officer *Commissioner of Patents and Trademarks*